United States Patent [19]

McKenzie

[11] Patent Number: 5,670,618
[45] Date of Patent: Sep. 23, 1997

[54] INSULIN-LIKE PEPTIDE

[75] Inventor: Maureen A. McKenzie, Far Hills, N.J.

[73] Assignee: The State University of New Jersey, Piscataway, N.J.

[21] Appl. No.: 507,124

[22] Filed: Aug. 18, 1995

Related U.S. Application Data

[63] Continuation of Ser. No. 956,342, Oct. 5, 1992, abandoned.
[51] Int. Cl.$^6$ .............................. A61K 38/28; C07K 14/00
[52] U.S. Cl. .......................... 530/303; 530/325; 530/326
[58] Field of Search ....................................... 530/303, 325, 530/326

[56] References Cited

U.S. PATENT DOCUMENTS 4,548,904  10/1985  Kent et al. .................................. 436/89

OTHER PUBLICATIONS

Results of search of SWISSPROT database with ScILP amino acid sequences as queries 1994.
Results of search of GENEMDL database using nucleotide sequence of cloned PCR product as query 1994.
Description of BLASTN and BLASTP search programs 1994.
LeRoith et al, Proc. Natl. Acad. Sci. USA, vol. 77, No. 10, pp. 6184–6188 (1980).
Rubinovitz et al, FEMS Microbiology Letters, vol. 29, pp. 53–58 (1985).
LeRoith et al, Can. J. Biochem. Cell Biol., vol. 63, pp. 839–849 (1985).
Thim et al., Proc. Natl. Acad. Sci., vol. 83, pp. 6766–6770 (1986).
LeRoith, D., et al. "Receptors for intercellular messenger molecules . . . ".
Kole, H., et al. FASEB Journal, vol. 5, Sep., 1991, pp. 2728–2734.
Lenard, J. TIBS-17, Apr., 1992, pp. 147–150.
Schieven, G., et al. Science, vol. 231, Jan. 24, 1986, pp. 390–395.
Nature, vol. 287, Oct. 30, 1980, pp. 782–787.
Rosen, O. Science, vol. 237, Sep. 18, 1987, pp. 1452–1457.
Petruzzelli et al., J. Biological Chem., vol. 260, Dec. 25, 1986, pp. 16072–16075.
Klebl et al. J. Bacteriol. 171(11):6259–6264, 1989.
McKenzie et al. 1990 J. Cell Biol. 111 (5 pt 2): 472A.
McKenzie et al 1992 Molec. Biol. Cell 3(Suppl):141A.
Robitzki et al 1989 EMBO J 8(10): 2905–2909.

*Primary Examiner*—Vasu S. Jagannathan
*Assistant Examiner*—Christine Saoud
*Attorney, Agent, or Firm*—Birch, Stewart, Kolasch & Birch, LLP

[57] ABSTRACT

A purified insulin-like protein (ILP) isolated from *Saccharomyces cerevisiae* is disclosed. The ILP has a molecular weight of approximately 6.4 kilodaltons and the amino acid sequence of the 22 amino terminal residues of the protein has been determined. Computer-assisted molecular graphics analysis of ILP illustrates the similarity of the sequenced portion to vertebrate insulin A-chains.

11 Claims, 7 Drawing Sheets

```
                         L
           A           C*S         P*
    ILP  VGVWPTDCSHYAAEKAALQTYCN*
           •        •  •  •    •••
          ••      •••  •• •   •• •••
  HUMAN   GIVE•QCCTSICSLYQLENYCN

L
           A           C*S         P*
    ILP  VGVWPTDCSHYAAEKAALQTYCN*
           •        •  •  •    •••
          ••      ••••  •• •   •• •••
 CHICKEN  GIVE•QCCHNTCSLYQLENYCN

L
           A           C*S         P*
    ILP  VGVWPTDCSHYAAEKAALQTYCN*
           •     •  •  •  •    ••  •••
          ••    ••••  •••     ••••••
TOADFISH  GIVE•QCCHRPCDKFDLQSYCN

L
           A           C*S         P*
    ILP  VGVWPTDCSHYAAEKAALQTYCN*
            •       •   ••      •••
          ••      •••   ••  •    •  •••
Geodia cydonium  IV••QQCTSGICSLYQ•ENYCNU L
           A           C*S         P*
    ILP  VGVWPTDCSHYAAEKAALQTYCN*
                •   ••          •   •
               ••  ••        •••  •    •
Neurospora crassa  LFS•PS•CSDLWTHTIVENYLYNL*
```

FIGURE 2

INSULIN-LIKE PEPTIDE

This application is a continuation of application Ser. No. 07/956,342 filed on Oct. 5, 1992, now abandoned.

CROSS-REFERENCE TO RELATED APPLICATIONS

This application is related to application Ser. No. 07/956,294, now abandoned entitled "INSULIN-DEPENDENT YEAST OR FUNGI" and Ser. No. 07/956,290, now U.S. Pat. No. 5,401,830 entitled "INSULIN RECEPTOR-LIKE PROTEIN", which were both filed on Oct. 5, 1992. The entire contents of both of these applications are hereby incorporated by reference.

BACKGROUND OF THE INVENTION

1. Field of the Invention

The invention relates to a polypeptide factor which demonstrates biochemical and physiological properties similar to mammalian insulin.

2. Description of the Related Art

Insulin effects on mammalian glucose homeostasis are well documented. Traditionally linked to a specialized endocrine organ such as the pancreas, insulin-like molecules have been assigned a more general role throughout the phyla. The major elements of glucose homeostasis are glycolysis and glycogen synthesis, two metabolic pathways that transcend more than a billion years of evolution. They agonize and antagonize one another to regulate and maintain the growth and viability of virtually all living systems. Therefore, boundaries of conventional wisdom that limit production and localization of hormones to endocrine glands and highly specialized target tissues may be too restrictive. Evidence for hormone synthesis without glandular localization comes from cells adapted to culture, diverse malignant cells derived from nonendocrine tissues, neurons from various organisms, and cells and tissues that emerged during very early stages of development.

Insulin may affect very primitive functions via ancient intracellular signaling systems. Literature citations spanning 15–20 years propose structural and functional homologs of vertebrate hormones in invertebrate and unicellular organisms. Indirect evidence includes metabolic responses, the existence of gene sequences, proteins and peptides, and their related controlling elements.

Knowledge of the physiologic function in invertebrates is further supported by ample evidence for insulin's role in regulation of reverse carbohydrate metabolism and reproductive activity in insects. Insulin has been identified in nerves, gut epithelium and possibly in other cells of invertebrate organisms that lack pancreatic islets such as insects, mollusks, worms and sponges. Recently, primary sequence data has been presented for an insulin-like substance, prothoracicotropic hormone found in the silkworm, *Bombyx morii*. Subsequently, a gene encoding an insulin-related peptide was identified in the sponge, *Geodia cydonium*. Elegant work resulted in the identification of an insulin receptor and cognate genomic sequence for an associated tyrosine kinase in the fruitfly, *D. melanogaster*.

An even simpler model, the yeast *Saccharomyces cerevisiae*, offers direct means to definitively assess events that couple ligand binding to receptor activation, formation of transient intermediates, and molecular targets of the activated receptor. For example, events proximal to insulin binding at the receptor can be traced to distal events, such as dephosphorylation of glycogen synthase or phosphorylation of ribosomal protein S6. Furthermore, the interactions of multiple mutations, their suppressors, and ultimately, the molecular participants in an insulin activated response, can be readily tested in yeast. The ease of biochemical, genetic and molecular biological manipulation has made *S. cerevisiae* an excellent model for study of metabolic control in eukaryotic cells.

However, hormones like paracrine/autocrine factors, and their respective cognate receptors, have proved more elusive in lower eukaryotes. To date, none of the above named hormone-like molecules from a microbial source have positive identification or chemical characterization. Downstream components analogous to those coupled in vertebrate hormone systems cover a wide range of metabolic regulatory functions previously considered exclusive to vertebrates.

TABLE I

Downstream Components of the Insulin Signalling Pathway

EFFECTOR PROTEINS

Insulin/Insulin Receptor
Tyrosine Protein Kinase(s)
Serine/Threonine Protein Kinase(s)
Protein Kinase C
cAMP-Dependent Protein Kinase (R/C Subunits)
Adenylate Cyclase
RAS and RAS-Like Proteins
G-Proteins (a, 0, y, Other p21s)
Phosphatase(s)
GAP (GTPase Activating Protein)
cAMP-Dependent Phosphodiesterase(s)
Phospholipase C
Phosphatidylinositol Kinase(s)
Calmodulin
Cell Division Cycle Protein (CDC25; Glucose Sensor)

LOW MOLECULAR WEIGHT EFFECTOR MOLECULES

Phosphatidylinositol-PhosphateGlycan (suggested)
Inositol Phosphates
Diacylglycerol (Myristate-Containing)
cAMP, CGMP
$Ca^{++}$ (Mobilization)
Fructose-2,6-Bisphosphate

ENZYMES REGULATED BY PHOSPHORYLATION/DEPHOSPHORYLATION

Cell Division Cycle Protein (CDC28/cdc2+/p34)
Glycogen Synthase, G-6-P D→1 (d)
Glycogen Phosphorylase/Phosphorylase Kinase (d)
Pyruvate Dehydrogenase (d)
ATP-Citrate Lyase (p)
Acetyl-CoA Carboxylase (p)
HMG-CoA Reductase (d)
Ribosomal Protein S6 (p)

The initial data associating insulin with lower eukaryotes was published during the early 1970's. Flawia and Torres first described the effects of bovine insulin on membrane-associated adenylate cyclase from *Neurospora crassa* (1,2). Insulin at low doses ($10^{-9}$M) was observed to significantly inhibit the specific activity of the fungal enzyme. Alternatively, glucagon, a documented antagonist of insulin under many physiological circumstances, stimulated adenylate cyclase activity (1,3). Later, preliminary studies performed by Legros and colleagues with the alga, *Acetabularia mediterranea*, suggested specific binding of the hormone to this organism (4). The group of Csaba observed a small effect of bovine insulin on glucose uptake in the protist, *Tetrahymena pyriformis* (5,6), and attributed this action to the presence of receptor molecules on the surface of these cells (6). Shortly thereafter, the influence of bovine insulin on the phosphotransferase system and growth rates of the prokaryote, *Escherichia coli*, was documented (7). Eventually, *E. coli* and other bacteria, were shown to produce insulin immunoreactive and bioreactive molecules (8,9).

Almost concomitant with the discovery of the bioeffects of vertebrate insulin on microbial metabolic processes, a substance was discovered that resembles vertebrate insulin in lower eukaryotes. During the beginning of the 1980's Roth and collaborators at the NIH described and partially characterized substances resembling vertebrate insulins in *T. pyriformis*, and in the filamentous fungi, *Aspergillus fumigatus* and *N. crassa* (10). Material extracted from cells and conditioned medium could be recovered as distinct peaks in the region characteristic of insulin (approximately 6 kD) by Sephadex G-50 gel filtration. Standard radioimmunoassay (RIA) for porcine insulin and a bioassay for lipid synthesis in rat adipocytes was used to detect activity eluting in column fractions. The gel-filtered material from Tetrahymena had reactivity in RIA approximately equal to its activity in the bioassay, whereas the Neurospora material displayed an immunoreactivity:bioactivity of 1:3. The activity that stimulated lipogenesis could be neutralized, though not completely, by anti-insulin antisera. For extracts derived from Tetrahymena or Neurospora, either 75–95% or approximately 60%, respectively, of the active component was neutralized by anti-insulin antibodies. The substance is presumably more similar to insulin than any other known, that is not insulin, and is nearly as well characterized as the circulating form of insulin in mammals. However, no biological effects of the partially purified material on lower eukaryotes have been published.

Conversely, biological effects of mammalian insulins have been observed in a cell wall-less strain of Neurospora. The addition of mammalian insulin to a nutritionally rich, chemically defined culture medium resulted in distinctively different morphology, enhanced growth, and extension of viability at the stationary phase in culture (11). Bovine, porcine, and recombinant human insulin had similar influence on growth and morphology, while proinsulin, reduced insulin, and several other proteins were inactive. Insulin added in the presence of excess anti-insulin antibody was without activity. These observations are consistent with the well-established role of insulin or related insulin-like growth factors, IGF-I and IGF-II, as a mitogen or differentiation inducing factor in hormonally defined media for mammalian cells in culture. Growth promotion and prolonged viability implies that nutritional metabolism, especially carbohydrate utilization, may be altered by the hormone. Experiments with these cells revealed that treatment with bovine insulin produced several significant effects on glycogen metabolism (12,13). For example, cells grown in the presence of 100 nM insulin possessed 40% more glycogen than did control cells. The incorporation of $^{14}$C-labelled glucose into glycogen increased 41% (p>0.01) after a 30 min treatment with the same concentration of insulin. Intracellular levels of the glycogen precursor, UDPG-glucose, were also determined by $^{31}$P-nuclear magnetic resonance (NMR) to increase in response to insulin.

SUMMARY OF THE INVENTION

The present invention is directed to a factor, yeast "insulin-like peptide" (ILP) which is secreted from yeast cells which demonstrates biochemical and physiological properties similar to mammalian insulins. The protein has been purified to homogeneity and antibodies to the protein have been obtained. The ILP has a molecular weight of approximately 6.4 kilodaltons and the amino acid sequence of the 22 amino terminal residues of the protein has been determined. Computer-assisted molecular graphics analysis of ILP illustrated the similarity of the sequenced portion to vertebrate insulin A-chains. This model suggests that ILP is able to bind to a mammalian insulin receptor in a manner similar to that by which mammalian insulin binds to the receptor. Interestingly, those amino acids which are involved in protein-protein interactions are conserved between ILP and bovine insulin. In yeast, rates of glycogen synthesis and growth are regulated in a reciprocal fashion (14), a phenomenon consistent with the dual role of insulin in mammals. ILP is produced during the transition from the lag to logarithmic phase of culture, supporting its role as a growth factor.

Accordingly, it is one object of the invention to provide an insulin-like protein (ILP), which has biochemical and physiological properties similar to those of mammalian insulin. The ILP has the following chemical, physical, biological, immunological and other properties:

Conventional and high performance size exclusion chromatography suggest that the intact protein possesses a molecular weight of 6.4±0.2 kDa.

Binding of ILP or mammalian insulin to an insulin-related receptor on a yeast cell stimulates glycogen synthesis under proper conditions.

The nearly homogeneous molecule stimulates autophosphorylation of the 95 kDa β-subunit of the insulin receptor kinase on tyrosine residues in H4 hepatoma cells.

Conversely, binding of mammalian insulin to an insulin receptor-like protein in yeast results in its autophosphorylation on tyrosine residues. A number of proteins which are called collectively "downstream effector" proteins are also tyrosine phosphorylated in response to insulin binding.

It is a further object of the invention to provide antibodies to yeast ILP.

It is a further object of the invention to provide chromatography matrices which comprise an insoluble matrix conjugated to the ILP or to an antibody which reacts with ILP.

It is a further object of the invention to provide a method for screening of compounds to identify compounds which inhibit the binding of ILP or of mammalian insulin to ILP receptor or to a mammalian insulin receptor.

It is a further object of the invention to provide compounds identified by such screening for competition for binding to the ILP receptor and to provide methods of treating a patient for an infection by an Ascomycete fungus by administration of such a compound.

BRIEF DESCRIPTION OF THE DRAWINGS

FIG. 2 is an alignment of the amino acid sequence of the 22 amino terminal proximal amino acids of ILP with the homologous residues of human insulin and insulin-like proteins from other species. (SEQ. ID. NOS.: 1–6)

DETAILED DESCRIPTION OF THE INVENTION

The ILP of the present invention was obtained from *Saccharomyces cerevisiae* strain S288c. However, ILPs from other yeast or fungi should be obtainable based on the teachings of this application. Other yeast and fungi include yeasts from the genera Saccharomyces, Schizosaccharomyces, Aspergillus, Penicillium, Neurospora, Candida, Torulaspora, and Torulopsis. Other species of *S. cerevisiae* may include *carlsbergensis* and *ellipsoidens var.* Various yeast and Fungi strains which may be useful are described in the American Type Culture Collection CATALOGUE OF FUNGI/YEASTS, Seventeenth Edition (1987). It should also be possible to obtain ILP by cloning the gene encoding ILP from yeast and expressing the ILP gene in a suitable host such as a yeast or bacteria.

The present invention also relates to recombinant DNA which encodes a whole or portion of ILP.

ILP is a peptide of 22 (or 23 if a tentative C-terminal asparagine is assigned) that displays 55–75% similarity (45% identity) with several vertebrate insulins and suggests the presence of a pathway in yeast that is closely related to one found in higher eukaryotes. To substantiate these assertions, experiments to identify and characterize the insulin-like peptide(s) in Saccharomyces have been performed. In addition to providing insight into the structure and properties of the ILP itself, the data obtained in these experiments can be used to isolate genes encoding ILP and related proteins in yeasts and other lower eukaryotes.

The scope of the present invention is described in the following experimental examples. These examples are intended to be illustrative, rather than limiting, of the scope of the invention.

EXAMPLE 1

Purification of the Insulin-like Peptide Secreted by *Saccharomyces cerevisiae* (ScILP)

Figure 1:
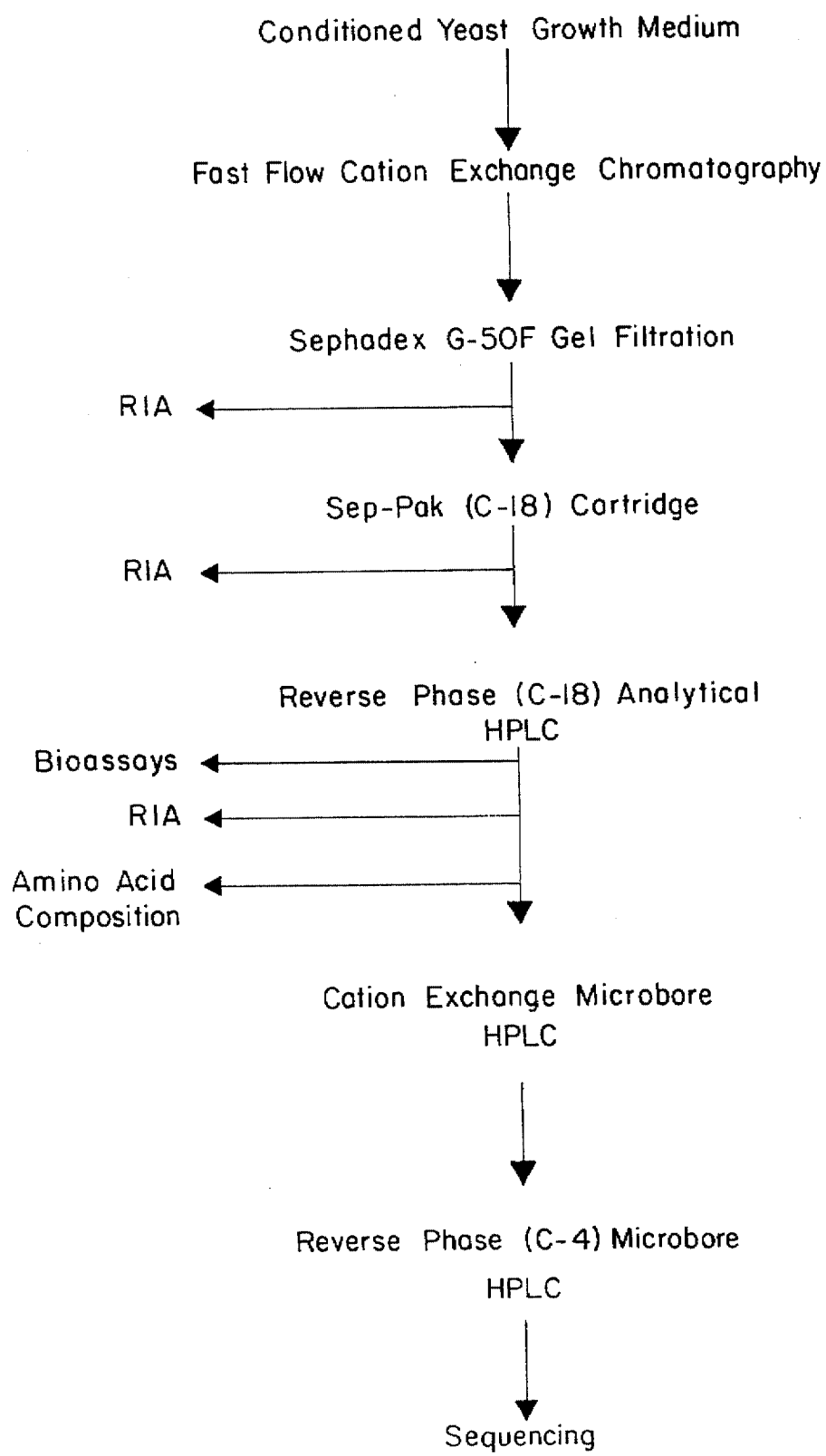
FIG. 1 is a flow chart diagram of the procedure used to purify the ILP of the present invention.
Figure 3A:
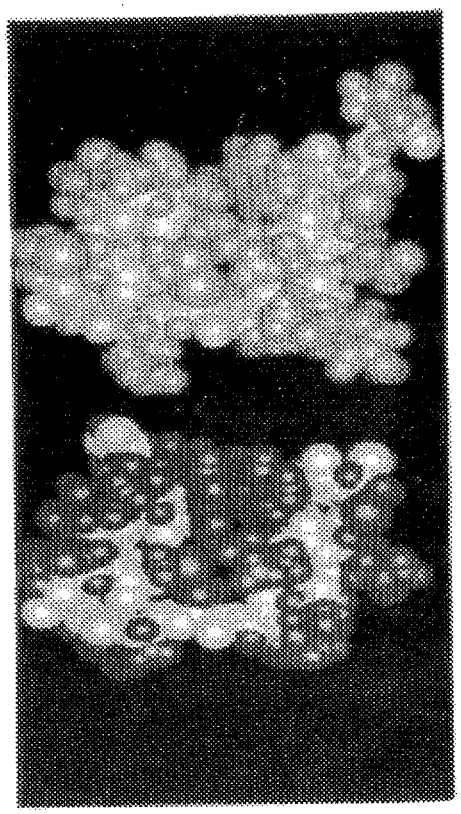
FIGS. 3A through 3E are computational graphics representations of the ILP.
Figure 3B:
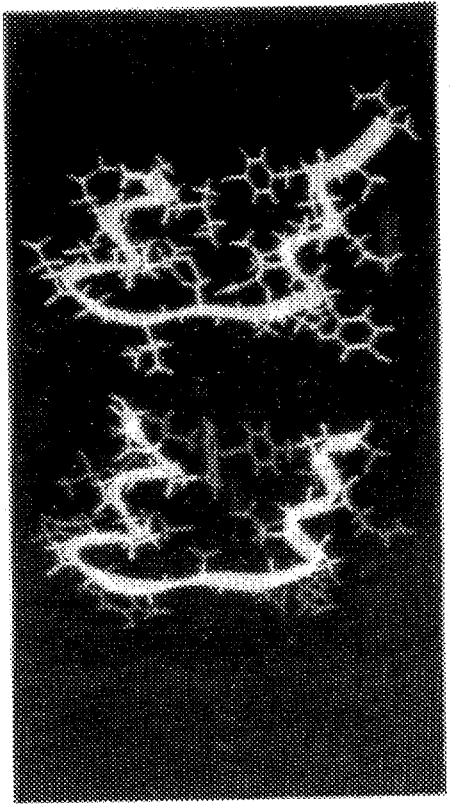
Figure 3C:
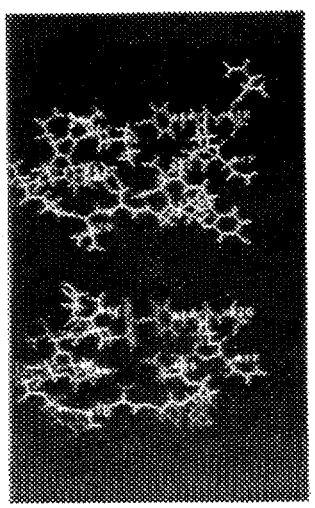
Figure 3D:
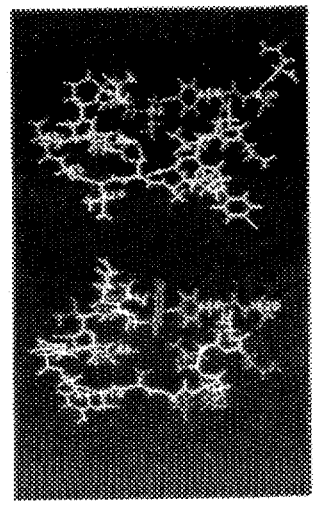
Figure 3E:
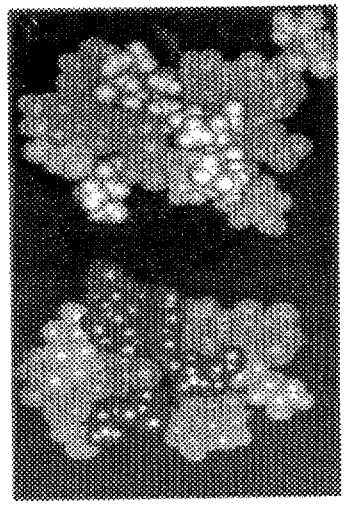

To completely characterize the primary and higher order structure of ScILP, large quantities of the peptide must be obtained. Approximately 1500 liters of fermentation broth were purified to develop the chromatographic scheme illustrated in FIG. 1.

For isolation of intracellular ILP, stock cultures of *S. cerevisiae* strain S288c (Fungal Genetic Stock Center strain X1280-1b; MATa SUC2 mal mel gal CUP1) were maintained on YNB (Yeast Nitrogen Base with ammonium sulfate and amino acids (Difco) plus dextrose (2%)) slants. Batch cultures were propagated in similar liquid medium (1–2 L), at 30° C. with shaking at 250 rpm for 18–24 hours. These starter cultures were used as an inoculum for 50–200 L fermenters containing YNB. The fermenters were operated at 30° C., with agitation to provide sufficient dissolved oxygen to support aerobic growth. The medium was maintained at pH 5.0 for the duration of the fermentation by dropwise addition of 50% aqueous ammonia. The fermentation was terminated after 14–16 hours of incubation, when the glucose supply, as monitored manually with Dextrostix (Ames), was exhausted.

The cells were separated at ambient temperature from the growth medium in a Sharples centrifuge. The cells and medium were placed at 4° C. prior to isolation of the insulin-like peptide (ILP). Cells were weighed, mixed with ice-cold 0.2N HCl and disrupted with a Manton-Gaulin laboratory homogenizer. The broken cells were suspended in 10 vol of ice-cold acid ethanol (0.2N HCl/75% ethanol) and mixed overnight at 4° C. The extracted suspension was centrifuged at 1500×g for 30 min. at 4° C. and the precipitate was discarded. The supernatant was concentrated (20–100×) by air evaporation at room temperature and was maintained at pH 1–2 by the addition of concentrated NaOH. The sample was reduced further (up to 400×) by lyophilization or in a Speed-Vac equipped with an acid trap at room temperature. The concentrate was centrifuged at 1500×g for 20 min at 4° C. and the precipitate was washed with 1 vol 1M $CH_3COOH$. After recentrifuging, the pellet was discarded and the supernate was applied to a Sephadex G-50F column equilibrated in 1M $CH_3COOH$ at 4° C. Fractions were collected, concentrated in a Speed-Vac to near dryness, washed 1× with a small volume of distilled water, and concentrated again to near dryness.

The G-50 eluate was concentrated on a Sep-pak C-18 (reverse phase) cartridge. The peptide was eluted from the Sep-pak with two volumes of 45% acetonitrile/$H_2O$/0.1% trifluoroacetic acid. The eluate was concentrated by vacuum evaporation to near dryness, adjusted to 12% acetonitrile/$H_2O$/0.1% trifluoroacetic acid and injected onto a Waters C-18 (reverse phase) analytical or semi-preparative HPLC column equilibrated in the same solvent system. The peptide was eluted from the column with a gradient of 12–44% acetonitrile/$H_2O$/0.1% trifluoroacetic acid. Eluted peptides were detected at 215 nm and 280 nm. Fractions (1 ml) were collected at a flow rate of 0.75 ml/min. Fractions appearing at 33–38 minutes were pooled and applied to a microbore HPLC system fitted with a sulfopropyl derivatized cation exchange resin ("PEPKAT", F. Herbst, University of Heidelberg, Germany). Buffer A was 5 mM $PO_4$, pH 3.0, buffer B was 1M NaCl in buffer A. The peptide was eluted with a linear gradient of 0 to 100% B over 60 minutes at ambient temperature. Peptide elution was monitored at 230 nm.

Yield of the ILP from the cells was minimal, consistent with the proposed secretion of the ILP. Accordingly, ILP was purified from culture supernatants as follows. All steps were performed at 4° C.

Cells were grown in 200 L YNBM culture medium supplemented with 10 mg/L histidine, 20 mg/L methionine, 20 mg/L tryptophan, 2% glucose, 5 g/L $(NH_4)_2SO_4$ in a fermenter as described above. Upon glucose exhaustion of the medium, cells were harvested by centrifugation and the clarified conditioned medium was adjusted to pH 3.5 with NaOH, unless the medium was maintained at pH 5.0 with aqueous ammonia throughout fermentation, and the pH was adjusted to 3.5 with HCl. The medium was concentrated by passing over a 300 ML bed of S-Sepharose Fast Flow (Pharmacia) equilibrated in 0.2M ammonium acetate, pH 3.5, at a flow rate of approximately 6 L/hr. The column was washed with 10 vol of the same buffer and the sample was eluted from the resin with 2 vol of the same buffer containing 0.1M NaCl. The eluate was further concentrated by vacuum evaporation to 10% of the original volume and adjusted to 1M acetic acid. This sample was applied to a Sephadex G50-F (Pharmacia) column ~1.2 L equilibrated in 1M acetic acid and 4–5 ml samples were collected at a flow rate of 1 ml/min. The G-50 eluate was concentrated on a Sep-pak C-18 (reverse phase) cartridge. The peptide was eluted from the Sep-pak with two volumes of 45% acetonitrile/$H_2O$/0.1% trifluoroacetic acid. The eluate was concentrated by vacuum evaporation to near dryness, adjusted to 12% acetonitrile/$H_2O$/0.1% trifluoroacetic acid and injected onto a Waters C-18 (reverse phase) analytical or semi-preparative HPLC column equilibrated in the same solvent system. The peptide was eluted from the column with a gradient of 12–44% acetonitrile/$H_2O$/0.1% trifluoroacetic acid. Eluted peptides were detected at 215 nm and 280 nm. Fractions (1 ml) were collected at a flow rate of 0.75 ml/min. Fractions appearing at 33–38 minutes were pooled and applied to a microbore HPLC system fitted with a sulfopropyl derivatized cation exchange resin ("PEPKAT", F. Herbst, University of Heidelberg, Germany). Buffer A was 5 mM$PO_4$, pH 3.0, buffer B was 1M NaCl in buffer A. The peptide was eluted with a linear gradient of 0 to 100% B over 60 minutes at ambient temperature. Peptide elution was monitored at 230 nm.

The highly purified peptide which eluted at approximately 30 min. was applied to a C4 microbore system and eluted in a gradient of Buffer A=0.1% TFA in $H_2O$/0.1% TFA gradient was 25–65% B over 60 minb. The peptide eluted at approximately 25–30 min. This sample was applied to an Applied Biosystems sequencer for determination of primary structure.

A 200 liter fermenter was processed through the scheme and yielded approximately 75 pmoles of highly purified ScILP for amino acid composition (Table II) and N-terminal sequence analysis. Amino acid analyses by diphenylhydantoin or O-pthalaldehyde procedures performed on three independent preparations of the peptide purified through the C-18 column step suggested that its composition fell within the range of variations known to vertebrate insulins.

TABLE II amino acid analyses of insulin-like proteins

| | lymnaea | lamprey | alligator | salamon | chicken | beef | yeast |
|---|---|---|---|---|---|---|---|
| asy | 3 | 4 | 5 | 6 | 4 | 3 | 8 |
| ser | 6 | 4 | 3 | 1 | 3 | 3 | 5 |
| gly | 3 | 7 | 5 | 4 | 4 | 4 | 5 |
| glx | 6 | 4 | 6 | 5 | 7 | 7 | 6 |
| thr | 3 | 4 | 1 | 0 | 1 | 1 | 4 |
| ala | 5 | 3 | 3 | 4 | 4 | 3 | 6 |
| val | 4 | 3–4 | 3 | 3 | 3 | 5 | 3 |
| met | 2 | 1 | 0 | 0 | 0 | 0 | 1 |
| tyr | 1 | 4 | 4 | 3 | 4 | 4 | 3–4 |
| ile | 2 | 1–2 | 1 | 2 | 1 | 1 | 3 |
| leu | 4 | 4 | 6 | 5 | 6 | 6 | 4 |
| phe | 2 | 2 | 2 | 3 | 2 | 3 | 2 |
| his | 1 | 3 | 2 | 3 | 3 | 2 | 1 |
| trp | 4 | 0 | 0 | 0 | 0 | 0 | 0 |
| lys | 1 | 2 | 1 | 3 | 1 | 1 | 3 |
| arg | 4 | 2 | 2 | 0 | 1 | 1 | 1–2 |
| pro | 4 | 1 | 1 | 2 | 1 | 1 | * |
| cys | 8 | 6 | 6 | 6 | 6 | 6 | * |

Sequencing was performed using Applied Biosystems Sequencer (University of Heidelberg, Germany) and revealed a peptide of 22 amino acids that was comparable to vertebrate insulin A chains (FIG. 2).

The peptide is apparently pure as evidenced by stretches of unique residue assignment. In those positions which are not uniquely assignable, the ambiguity in amino acid assignment most likely represents true heterogeneity in the sequence of the protein.

Failure to identify this protein in any of the gene/protein data banks implies that this peptide, or larger protein from which it may be derived, is not known. The algorithm of Needleman and Wunsch (15), attaches weight values to pairs of amino acids in the analysis, and compares between species the number of bases conserved within the codons (none to all three), was employed to trace the possible evolutionary development of the peptide. According to calculations based on this algorithm, the primary sequence and the unknown yeast molecule and the A-chain moiety of evolutionarily diverse vertebrate insulins were 55–75% similar (45% identical) in the absence or presence of only one gap introduced to improve alignment. Comparison of the 22-residue sequence to vertebrate insulin B-chains showed a 45–65% similarity, but several gaps were required to achieve this likeness. (If the tentative C-terminal asparagine is assigned, the likeness is improved). It should be noted that certain features of the ILP molecule appear to be strongly conserved in evolutionarily distant organisms such as yeast and vertebrates. Conserved residues are found in the primary sequence at GlyA2 (adjusted with a gap to correspond to vertebrate GlyA1, CysA6, LeuA16, TyrA19 and CysA20). Conservative substitutions are also found in the molecule in residues ValA3 (adjusted with the same gap as above to correspond to vertebrate IleA2, AspA7, SerA9, HisA10, AlaA12, GluA14, LysA15, GlnA17, and ThrA18). Many of these residues strongly influence the structure, specificity, and potency of biologically active insulin or the related insulin-like growth factors.

Computer-assisted molecular graphics demonstrated the facility with which the proposed ScILP primary sequence could assume the conformation of the porcine insulin A-chain (FIG. 3). The X-ray crystallographic coordinates reported by Wlodowa et al (16) for the porcine insulin A-chain residues were used as a model. The backbone conformation was constrained and ILP residues were simply substituted into the respective porcine amino acid positions. In this analysis, steric hindrance or "bumping" of amino acid side chains was not observed. Thus, it would appear that the structure assumed by ScILP is likely to resemble insulin in its preferred conformation. The residues of vertebrate insulin proposed to be involved in receptor binding are GlyA1 and, in ScILP, GlyA1 of porcine insulin occurs as GlyA2. The modified spatial orientation should still allow access for H-bonding to a typical insulin receptor. TyrA19 is completely conserved in ScILP. This residue is implicated in molecular stabilization as well as in receptor binding. IleA2, also involved in structural stability, is present as IleA3 in ScILP. The CysA6 and CysA20, presumed to be extremely important in the structure, storage and processing of insulin have been tentatively assigned to the identical position in ScILP. The importance of these residue positions makes their relative functional and structural conservation exciting. FIG. 3 illustrates possible ScILP structural conformations (a–e). The constrained peptide backbone is similar (a: space filling and b: ribbon); conservative substitutions, conserved functional residues, and porcine IleA2 is compared to yeast IleA3; the antibody binding site (d:); distribution of surface contacts and charges (e:). The clustering of hydrophobic residues within the center of the insulin molecules is hypothesized to modulate its biological activity and potency (10). The mechanism is thought to involve $Zn^{++}$ binding primarily mediated by B-chain residues, SerB9 and HisB10, and by hydrophobic interactions between cores comprised of both chains. The interaction occurs at relatively high concentrations of insulin in solution. Importantly, ScILP possess a central core of hydrophobic residues (FIG. 3). It aggregates readily to form dimers, tetramers and hexamers from monomers, as displayed on HPLC sizing columns, potentially through the SerA9 and HisA10 as binding sites for $Zn^{++}$.

These results may indicate the presence of a B-chain moiety in ScILP, as found in vertebrates. The unassigned residues indicated by amino acid composition are coincidentally predominant in the B-chain of phylogenetically disparate insulins and insulin-like growth factors and relaxin (10). Alternatively, microheterogeneous ScILP peptides may be encoded by discrete genes. Precedence for multiple copies of genes with overlapping functions are common in S. cerevisiae. A few involved in glucose metabolism and sensing genes that encode GTP binding or "G-proteins" and RAS1 and RAS2; phosphodiesterases PDE1 and PDE2 and; catalytic subunits of the cAMP-dependent protein kinase TPK1, TPK2, and TPK3.

Furthermore, the crossreactivity in binding assays of insulin and IGF-I suggests that the signal transduction pathway in yeast is not simply related to insulin. Schuster et al have documented similar sensitivity of yeast to expression of mammalian IGF-I (J. Schuster, Chiron Corp., Emeryville, Calif.; 17). V. Sara and co-workers (Department of Pathology, Karolinska Institutet, Stockholm, Sweden) have observed that mild expression of mammalian IGF-II gene in Saccharomyces causes the cells to rapidly lose viability (personal communication). Since alterations in a number of variables to control or alleviate technical problems proved unsuccessful, the conclusion was reached that some unknown physiological parameters had been perturbed in the yeast. The basis for these observations must be investigated in more detail but one may imagine that heterogeneous or multiple insulin-like receptors, in either specificity, affinity, or downstream functions, are present in S. cerevisiae. If true, it is tempting to speculate that more than one receptor gene product is present in these cells.

EXAMPLE 2

Antibodies to ILP

Antibodies were produced under contract by Antibody Resources, Incorporated, Rockville, Md. A synthetic peptide having the sequence AGVWPTDCSHYAAELAALQTYCN (SEQ. ID. NO.:1–12) was made using a peptide synthesizer (Johns Hopkins School of Medicine, Laboratory of Microchemistry). The peptide was conjugated to bovine serum albumin and the conjugate was used to raise polyclonal antisera in guinea pigs. Of three animals immunized, to date one has shown an antibody response as demonstrated by ELISA.

Antibodies to ScILP may be used either as detection or as purification reagents. As detection reagents, the use of antisera in a variety of formats, such as Western blotting, ELISA and radioimmunoassay are well known in the art. As a purification reagent, the antibody can be purified from the serum, for example by protein-G affinity chromatography (e.g. GIBCO BRL catalog number 5921SA) and then covalently conjugated to an insoluble chromatography matrix (e.g. CNBr-Sepharose, Pharmacia). Immunoaffinity chromatography protocols well known in the art, perhaps modified slightly as might be required for optimizing the purification, are then applied to purify the ILP from a yeast culture.

EXAMPLE 3

Cloning of a Gene Encoding ILP from *Saccharomyces cervisiae*

A gene encoding the ILP is being isolated by screening of a genomic library from *Saccharomyces cerevisiae* using degenerate oligonucleotide probes derived from the ILP amino acid sequence. The genomic library is obtained from Stratagene (San Diego, Calif.) and was made from DNA from S. cerevisiae strain S288c using the Lambda-DASH™ vector (catalog number 943901). The library is maintained in EPICURIAN COLI™ SURE™ bacteria, also a product of Stratagene.

Approximately $1 \times 10^7$ phage were screened using the degenerate oligonucleotide

5'-GARAARGCIGCIYTICARACITAYTGYAAY-3' (SEQ. ID. NO.:7).

The oligonucleotide mixture was labelled by 5'-end labelling with $^{32}PO_4$, using standard reaction conditions. Screening conditions were determined as described in Maniatis et al (18).

Additional experiments were performed using a panel of shorter degenerate oligonucleotides derived from five amino acid long sequences of the ILP. In these experiments, a Southern blot was performed using yeast DNA and molecular weight markers derived from Lamda DNA. This blot is run to assess the specificity of probe binding; conditions for screening are adjusted to provide specific banding in the yeast DNA while preventing probe binding to Lamda DNA. The positive clones obtained from the phage library identified by the first probe are then screened using the second panel of additional oligonucleotides under the appropriate conditions.

5'-GTNTGGCCNACNGAT-3' (SEQ. ID. NO.:8)

5'-GTNTGGCCNACNAAC-3' (SEQ. ID. NO.:9)

5'-GTNTGGCCNACNAAT-3' (SEQ. ID. NO.:10)

Those clones which specifically hybridize with the first oligonucleotide and at least one of the second oligonucleotides are considered to contain gene sequences which encode ILP.

The inserts contained within each of the thus identified lambda clones are completely characterized with respect to restriction map and those fragments which are found to contain DNA encoding ILP or a portion thereof are sequenced completely.

EXAMPLE 4

Expression of Cloned ILP

Yeast strains harboring disrupted null alleles of ScILP genes can be constructed according to standard methods (19, 20). Attenuated alleles can be created essentially as reported by Kataoka et al (21) for RAS genes from S. cerevisiae. Overexpression alleles under the control of the ADH1 (alcohol dehydrogenase) or the GALLO (galactose permease) high-copy promoters can be assembled as previously described (22–24). The gene can be overexpressed in E. coli (18), Schizosaccharomyces pombe or S. cerevisiae.

EXAMPLE 5

Screening for Compounds which Abrogate the Response of the Binding of Insulin-like Proteins to their Receptors As described above, the binding of ScILP to its receptor triggers physiological responses which are analogous to the responses which occur in mammalian cells upon binding of insulin, or of insulin-like growth factor, to their respective receptors. Thus, the interaction between ScILP and its receptor in the plasma membrane of the yeast can be used as a model system to develop compounds which abrogate the physiological response of the binding of insulin-like factors to their receptors.

The purified receptor for ScILP is the subject matter of co-pending U.S. patent application Ser. No. 07/956,290 entitled "INSULIN RECEPTOR-LIKE PROTEIN", which is herein incorporated in its entirety by reference.

Compounds which abrogate the cellular responses to the binding of a ligand to its receptor can affect the response either by preventing binding of the ligand to the receptor or by inhibiting the downstream events occurring after ligand binding. Formats for measuring competition for receptor sites between the normal ligand and an inhibitory compound are commonly known in the art. The most commonly used assay measures displacement of radiolabelled ligand by unlabelled competitor. In a typical experiment of this sort, one would label the ScILP protein with a radioisotope and measure the amount of label bound to a fixed amount of the receptor at increasing concentrations of unlabelled ScILP protein. Inasmuch as the receptor for ScILP is localized in the plasma membrane of the yeast cell, the receptor can be provided as either purified protein or on yeast cells.

The binding data describes the binding affinity of the receptor, expressed as a dissociation constant that indicates the concentration of ILP required to bind one-half of the available receptor molecules. One then performs this binding assay in the presence of increasing amounts of the unlabelled competitor. Those compounds which result in a significant increase in the amount of ScILP required to provide half-maximal saturation of the receptor are considered to be effective competitors of the ligand-receptor interaction.

Figure 4:
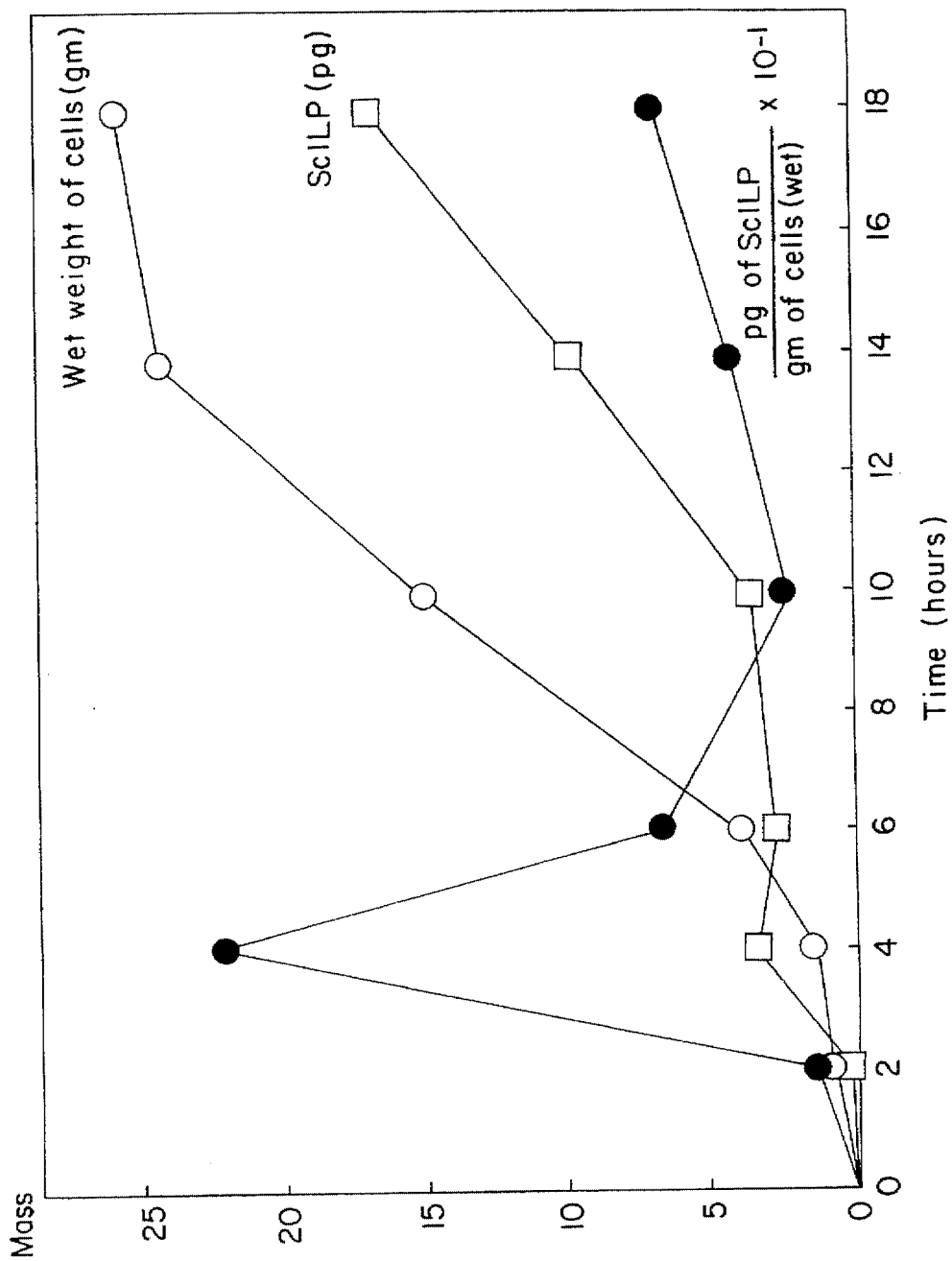
FIG. 4 presents the amount of ILP isolated from yeast culture supernatants as a function of time in culture.

Screening for compounds which inhibit processes occurring downstream of the receptor binding event can be assayed by adding the compound of interest to a culture medium in which the yeast are maintained and then providing the ILP protein to the culture. Aliquots of the cells are withdrawn at various times following the addition of the insulin-like factor and various biochemical tests are performed. For example, tyrosine phosphorylation of the receptor and its substrates, glycogen synthesis, cell growth rates, and mating and sporulation ability can be measured. The observation that ILP is maximally secreted by yeast just at the onset of exponential growth of a culture (FIG. 4) suggests that comparing the growth rate of cultures with and without ILP to cultures containing ILP and the potential inhibitor provides a global assay for effects of the compound upon physiological events downstream of ILP or other insulin-like proteins binding to their receptors.

In a preliminary experiment, the binding of labelled porcine insulin or of insulin-like growth factor (IGF-I) to yeast cells is demonstrated. Insulin binding studies with intact logarithmic and stationary phase yeast cells were performed under typical conditions for mammalian cells (25,26). In logarithmic phase yeast, porcine $^{125}$I-insulin binding had reached apparent equilibrium by 1–2 h and represented ca. 0.5% of the total counts specifically bound (FIG. 2a). At this time, greater than 95% of the labelled insulin appeared to be intact, as judged by TCA precipitable counts. Unlabelled porcine insulin displaced labelled insulin from intact yeast cells in a dose dependent fashion with 50% bound occurring around $10^{-9}$M (FIG. 2b). This value is in good agreement with the value obtained for displacement of insulin from mammalian cells. Results of binding studies with stationary phase cells treated similarly to logarithmic phase cells did not display typical displacement. Binding assays performed with isolated plasma membranes demonstrated high affinity binding sites for insulin ($K_d$=0.7 nM) and for IGF-I ($K_d$=0.4 nM), in good agreement with binding and displacement of insulin tracer from whole cells. Solubilized and wheat germ column purified plasma membrane preparations (27) from S. cerevisiae improved the results, and a greater percentage of the total insulin and IGF-I was shown to bind specifically (ca. 1–2% of 4–5% total binding) under comparable conditions.

EXAMPLE 6

Variants of the ILP

Cloned DNA encoding the ILP can be mutated in a site-specific fashion by any of the techniques well known in the art. Most of these methods employ hybridization of one or more oligonucleotide having mismatches with the template at specific nucleotides to be mutated. Hybridization of the oligonucleotide is followed by primer extension, either as a single sythetic round to completely copy a single-stranded template or as a polymerase chain reaction. Mutants are then selected by preferential hybridization of an oligonucleotide containing the mutation and confirmed by DNA sequencing. Larger insertions, deletions and fusions can be made by methods well known in the art of recombinant DNA technology.

Variants in ILP can be tested for biological activity in a number of assays and can also be evaluated in the computer model of the mammalian insulin-insulin receptor complex as described above. Two particularly useful activity assays are the stimulation of glycogen synthesis in yeast and stimulation of phosphotyrosine synthesis in mammalian proteins. Binding of the variant ScILP to the yeast insulin-like protein receptor and/or measurement of the ability of the variant to displace ILP or other insulin-like peptides from the ILP receptor would also be important data to obtain.

Figure 5:
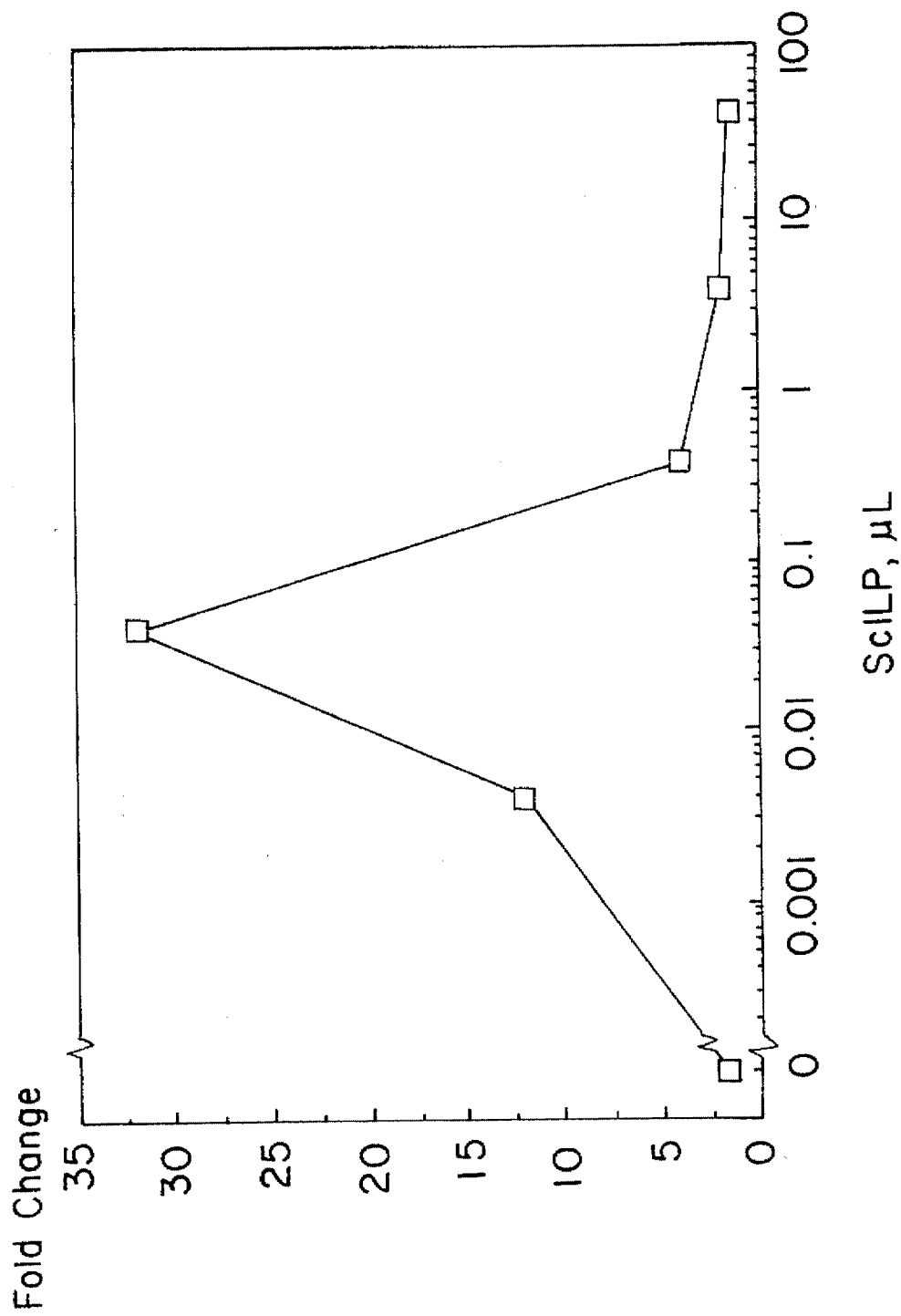
FIG. 5 shows the stimulation of glycogen synthesis in cultured yeast by various amounts of ILP.

To assay the effect of ScILP on glycogen synthesis, stationary phase cells are preincubated in phosphate buffer with various doses of ScILP (or a variant thereof). After 30 min of incubation in the presence of 1% glucose and uniformly labelled $^{14}$C-glucose, the cells are pelleted, resuspended in sodium carbonate, neutralized with HCl and treated with α-amylase to release the glucose incorporated into the newly synthesized glycogen. The enzymatically released glucose is collected and quantitated by scintillation counting. The optimal dose of ScILP (calculated to be ca. 10 pM) increases nascent glycogen 32-fold over basal levels compared to controls which displayed a 2-fold increase in glycogen compared to basal samples (FIG. 5).

Figure 6:
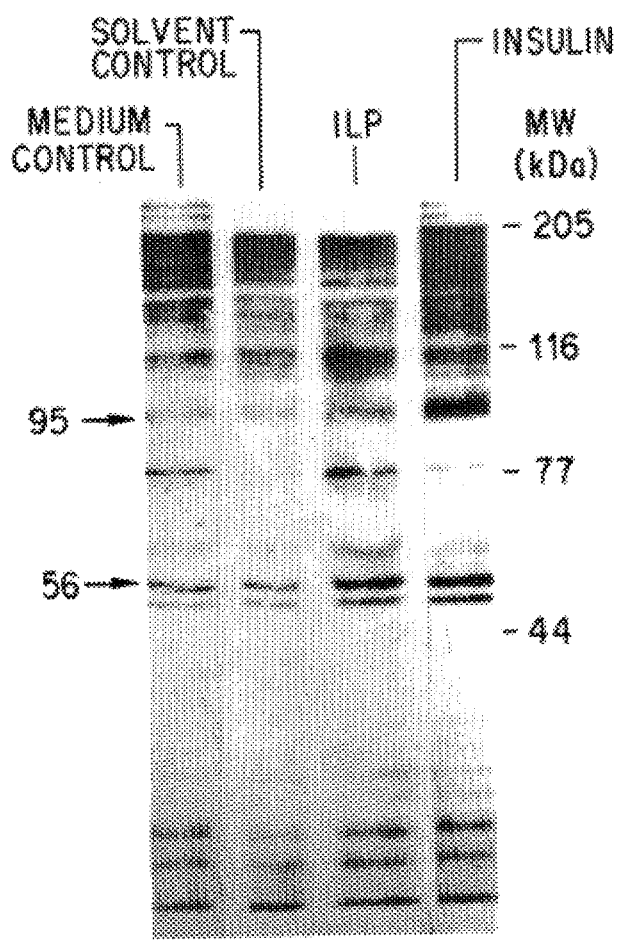
FIG. 6 shows the stimulation of protein tyrosine phosphorylation in H4 tissue culture cells in response to added ILP.

It has also been found that yeast ILP is able to cause protein phosphorylation on tyrosine in mammalian cells. In this experiment, H4 cells were grown in RPMI medium or RPMI with insulin or RPMI with ILP. Cells were washed and collected and lysed in Laemmli gel loading buffer. Total soluble proteins were separated by SDS-polyacrylamide gel electrophoresis and Western blotted using an anti-phosphotyrosine antibody. As shown in FIG. 6, Fractions containing partially purified ILP stimulated tyrosine phosphorylation of a 56 and a 95 kDa protein compared to the basal levels seen with solvent or uninoculated medium alone. Two additional proteins, of molecular weight, not observed to be tyrosine phosphorylated in the basal medium, are also tyrosine phosphorylated upon treatment with ScILP.

EXAMPLE 7

Treatment of Fungal Infections Using Compounds which Inhibit Insulin-like Protein Mediated Growth of the Fungus The methods of Example 3 can be employed to identify compounds which would inhibit growth of fungal infections. As noted above, the binding of ILP to its receptor stimulates growth of the yeast. It would be expected that compounds which interfere with the physiological processes which lead from receptor binding by ILP to the entry of cells into the cell cycle would be useful in the treatment of fungal infections. Accordingly, one might treat a patient with a composition containing an amount of a compound which inhibits growth of the fungus by inhibiting ILP receptor binding or downstream events sufficient to provide such inhibition in the clinical setting. The compound would most preferably be administered in a topical fashion, mixed with a pharmaceutically acceptable excipient and/or diluent, which encompasses eyedrops and aerosols, in addition to creams and lotions.

The invention being thus described, various modifications of the materials and methods employed in the Examples will be apparent to one skilled in the art. Such modifications are to be considered as falling within the scope of the invention as claimed below.

REFERENCES

Each of the references listed below is cited in the above disclosure and is hereby incorporated in its entirety by such citation. 1. M. M. Flawia and H. N. Torres, J. Biol. Chem. 248:4517 (1973). 2. M. M. Flawia and H. N. Torres, FEBS Lett. 30:74 (1973). 3. M. M. Flawia and H. N. Torres, Proc. Natl. Acad. Sci. USA 69:2870 (9172). 4. F. Legros et al., Protoplasma 86:119 (1975). 5. G. Csaba and T. Lantos, Experientia 31:1097 (1975). 6. G. Csaba et al., Protoplasma 91:179 (1977). 7. M. Abou-Sabe and T. Reilly, Biochim. Biophys. Acta 542:442 (1978). 8. D. LeRoith et al., Can. J. Biochem. Cell Biol. 63:839 (1985). 9. C. Rubinovitz and J. Shiloach, FEMS Lett. 29:53 (1985). 10. D. LeRoith et al., Proc. Natl. Acad. Sci. USA 85:6184 (1980). 11. M. A. McKenzie et al., Endocrinology 122:511 (1988). 12. S. E. Fawell et al., Endocrinology 122:518 (1988). 13. N. J. Greenfield et al., Biochemistry 27:8526 (1988). 14. V. L. A. Costa-Carvalho et al., Biotechnology Letters 8:57 (1986). 15. S. B. Needleman and C. D. Wunsch, J. Mol. Biol. 48:443 (1970). 16. A. Wlodawa et al., Rutgers University Computational Chemistry Database. 17. J. R. Shuster et al., Gene 83:47 (1989). 18. J. Sambrook et al., *Molecular Cloning, A Laboratory Manual*, 2nd edition, c. 1989 by Cold Spring Harbor Laboratory Press, Cold Spring Harbor, N.Y. 19. G. Boguslawski, "Yeast Transformation", pp. 161–196 in *Gene Manipulations in Fungi*, J. W. Bennett and L. L. Lasure, eds.; c. 1985 by Academic Press, New York, N.Y. 20. D. Botstein and R. W. Davis, "Principles and Practice of Recombinant DNA Research in Yeast", pp. 607–636 in *The Molecular Biology of the Yeast Saccharomyces: Metabolism and Gene Expression*, J. N. Strathern et al., eds., c. 1982 by Cold Spring Harbor Laboratory Press, Cold Spring Harbor, N.Y. 21. T. Kataoka et al., Cell 37:437 (1984). 22. J. Rine, Meth. in Enzymol. 194:239 (1991). 23. J. R. Broach et al., "Vectors for High-level Inducible Expression of Cloned Genes in Yeast", pp. 83–177 in *Experimental Manipulation of Gene Expression*, M. Inouye, ed., c. 1983 by Academic Press, New York, N.Y. 24. J. C. Schneider and L. Guarente, Meth. in Enzymol. 194:373 (1991). 25. J. Roth, Meth. in Enzymol. 37:66 (1975). 26. D. Feldman et al., Science 224:1109 (1984).

What is claimed is:

1. A purified protein which comprises a polypeptide that binds specifically to a yeast insulin-like protein receptor and which is isolated from a yeast culture, wherein said protein has a molecular weight of 6400±200 daltons, as determined by gel filtration chromatography.

2. The purified protein of claim 1, which is isolated from a Saccharomyces yeast.

3. The purified protein of claim 2, which is isolated from *Saccharomyces cerevisiae*.

4. A purified protein of claim 1, which upon binding to said yeast insulin-like protein receptor protein causes phosphorylation on a tyrosine residue of said yeast insulin-like protein receptor protein.

5. A purified protein as in claim 1, which elicits calcium mobilization upon binding to said insulin-like protein receptor protein.

6. A purified protein as in claim 1, which stimulates growth under appropriate nutrient conditions, glycogen synthesis and glucose utilization.

7. The purified protein of claim 1, which comprises an amino acid sequence selected from the group consisting of VGVWPTDCSHYAAEKAALQTYCN (SEQ. ID. NO.:11), AGVWPTDCSHYAAEKAALQTYCN (SEQ. ID. NO.:12), VGVWPTDCSHYACAEKAALQTYCN (SEQ. ID. NO.:13), VGVWPTDCSHYAAESAALQTYCN (SEQ. ID. NO.:14), VGVWPTDCSHYAAELAALQTYCN (SEQ. ID. NO.:15), VGVWPTDCSHYAAEKAALQTYPN (SEQ. ID. NO.:16), AGVWPTDCSHYACAEKAALQTYCN (SEQ. ID. NO.:17), AGVWPTDCSHYAAESAALQTYCN (SEQ. ID. NO.:18), AGVWPTDCSHYAAELAALQTYCN (SEQ. ID. NO.:19), AGVWPTDCSHYAAEKAALQTYPN (SEQ. ID. NO.:20), VGVWPTDCSHYACAESAALQTYCN (SEQ. ID. NO.:21), VGVWPTDCSHYACAELAALQTYCN (SEQ. ID. NO.:22), AGVWPTDCSHYACAESAALQTYCN (SEQ. ID. NO.:23), AGVWPTDCSHYACAELAALQTYCN (SEQ. ID. NO.:24), VGVWPTDCSHYACAEKAALQTYPN (SEQ. ID. NO.:25), AGVWPTDCSHYACAEKAALQTYPN (SEQ. ID. NO.:26), VGVWPTDCSHYACAESAALQTYPN (SEQ. ID. NO.:27), VGVWPTDCSHYACAELAALQTYPN (SEQ. ID. NO.:28), AGVWPTDCSHYACAESAALQTYPN (SEQ. ID. NO.:29), AGVWPTDCSHYACAELALQTYPN (SEQ. ID. NO.:30), VGVWPTDCSHYAAESAALQTYPN (SEQ. ID. NO.:31), VGVWPTDCSHYAAELAALQTYPN (SEQ. ID. NO.:32), AGVWPTDCSHYAAESAALQTYPN (SEQ. ID. NO.:33) or AGVWPTDCSHYAAELAALQTYPN (SEQ. ID. NO.:34).

8. A purified protein which comprises an amino acid sequence that is VGVWPTDCSHYAAEKAALQTYCN (SEQ. ID. NO.:11), AGVWPTDCSHYAAEKAALQTYCN (SEQ. ID. NO.:12), VGVWPTDCSHYACAEKAALQTYCN (SEQ. ID. NO.:13), VGVWPTDCSHYAAESAALQTYCN (SEQ. ID. NO.:14), VGVWPTDCSHYAAELAALQTYCN (SEQ. ID. NO.:15), VGVWPTDCSHYAAEKAALQTYPN (SEQ. ID. NO.:16), AGVWPTDCSHYACAEKAALQTYCN (SEQ. ID. NO.:17), AGVWPTDCSHYAAESAALQTYCN (SEQ. ID. NO.:18), AGVWPTDCSHYAAELAALQTYCN (SEQ. ID. NO.:19), AGVWPTDCSHYAAEKAALQTYPN (SEQ. ID. NO.:20), VGVWPTDCSHYACAESAALQTYCN (SEQ. I.D. NO.:21), VGVWPTDCSHYACAELAALQTYCN (SEQ. ID. NO.:22), AGVWPTDCSHYACAESAALQTYCN (SEQ. ID. NO.:23), AGVWPTDCSHYACAELAALQTYCN (SEQ. ID. NO.:24), VGVWPTDCSHYACAEKAALQTYPN (SEQ. ID. NO.:25), AGVWPTDCSHYACAEKAALQTYPN (SEQ. ID. NO.:26), VGVWPTDCSHYACAESAALQTYPN (SEQ. ID. NO.:27), VGVWPTDCSHYACAELAALQTYPN (SEQ. ID. NO.:28), AGVWPTDCSHYACAESAALQTYPN (SEQ. ID. NO.:29), AGVWPTDCSHYACAELALQTYPN (SEQ. ID. NO.:30), VGVWPTDCSHYAAESAALQTYPN (SEQ. ID. NO.:31), VGVWPTDCSHYAAELAALQTYPN (SEQ. ID. NO.:32), AGVWPTDCSHYAAESAALQTYPN (SEQ. ID. NO.:33) or AGVWPTDCSHYAAELAALQTYPN (SEQ. ID. NO.:34), wherein said protein binds specifically to a yeast insulin-like protein receptor, which is isolated from a yeast culture, which has a molecular weight of 6400±200 daltons, which upon binding to said yeast insulin-like protein receptor causes phosphorylation on a tyrosine residue of said yeast insulin-like protein receptor, and which elicits calcium mobilization upon binding to said insulin-like protein.

9. A purified protein as in claim 1, which comprises an amino acid sequence selected from the group consisting of VGVWPTDCSHYAAEKAALQTYCN (SEQ. ID. NO.:11), AGVWPTDCSHYAAEKAALQTYCN (SEQ. ID. NO.:12), VGVWPTDCSHYAAESAALQTYCN (SEQ. ID. NO.:14), AGVWPTDCSHYAAELAACQTYCN (SEQ. ID. NO.:19), VGVWPTDCSHYAAELAALQTYCN (SEQ. ID. NO.:15), and AGVWPTDCSHYAAESAALQTYCN (SEQ. I.D. NO.:18).

10. A purified protein which comprises the amino acid sequence VGVWPTDCSHYAAEKAALQTYCN (SEQ. I.D. NO. 11) and has an apparent molecular weight of 6400±200 daltons when measured by gel filtration chromatography.

11. A purified protein of claim 8, which comprises the amino acid sequence VGVWPTDCSHYAAEKAALQTYCN (SEQ. I.D. NO. 11).

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( i x ) FEATURE:
        ( A ) NAME/KEY: Peptide
        ( B ) LOCATION: 1..23
        ( D ) OTHER INFORMATION: /label=peptide
            / note="yeast insulin-like peptide"

( i x ) FEATURE:
        ( A ) NAME/KEY: Modified-site
        ( B ) LOCATION: 1..23
        ( D ) OTHER INFORMATION: /label=heterogeneity
            / note="Residue 1 can also be alanine. Residue 13
            can also be cysteine (insert), Residue 15 can also be
            serine or leucine. Residue 22 can also be proline."

( x i ) SEQUENCE DESCRIPTION: SEQ ID NO:1:

```
Val  Gly  Val  Trp  Pro  Thr  Asp  Cys  Ser  His  Tyr  Ala  Ala  Glu  Lys  Ala
 1                  5                        10                       15

Ala  Leu  Gln  Thr  Tyr  Cys  Asn
                 20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (v) FRAGMENT TYPE: N-terminal (v i) ORIGINAL SOURCE:
    (A) ORGANISM: Homo sapiens (i x) FEATURE:
    (A) NAME/KEY: Peptide
    (B) LOCATION: 1..21
    (D) OTHER INFORMATION: /label=peptide
       / note="Amino terminal sequence of human insulin A-chain"

(x i) SEQUENCE DESCRIPTION: SEQ ID NO:2:

```
Gly Ile Val Glu Gln Cys Cys Thr Ser Ile Cys Ser Leu Tyr Gln Leu
 1               5                  10                  15

Glu Asn Tyr Cys Asn
            20
```

(2) INFORMATION FOR SEQ ID NO:3:

(i) SEQUENCE CHARACTERISTICS:
       (A) LENGTH: 21 amino acids
       (B) TYPE: amino acid
       (C) STRANDEDNESS: single
       (D) TOPOLOGY: linear (i i) MOLECULE TYPE: peptide (i i i) HYPOTHETICAL: NO (v) FRAGMENT TYPE: N-terminal (v i) ORIGINAL SOURCE:
       (A) ORGANISM: chicken (i x) FEATURE:
       (A) NAME/KEY: Peptide
       (B) LOCATION: 1..21
       (D) OTHER INFORMATION: /label=peptide
         / note="Amino-terminal sequence of chicken insulin- like protein"

(x i) SEQUENCE DESCRIPTION: SEQ ID NO:3:

```
Gly Ile Val Glu Gln Cys Cys His Asn Thr Cys Ser Leu Tyr Gln Leu
 1               5                  10                  15

Glu Asn Tyr Cys Asn
            20
```

(2) INFORMATION FOR SEQ ID NO:4:

(i) SEQUENCE CHARACTERISTICS:
       (A) LENGTH: 21 amino acids
       (B) TYPE: amino acid
       (C) STRANDEDNESS: single
       (D) TOPOLOGY: linear (i i) MOLECULE TYPE: peptide (i i i) HYPOTHETICAL: NO (v) FRAGMENT TYPE: N-terminal (v i) ORIGINAL SOURCE:
       (A) ORGANISM: toadfish (i x) FEATURE:
       (A) NAME/KEY: Peptide
       (B) LOCATION: 1..21
       (D) OTHER INFORMATION: /label=peptide
         / note="Amino-terminal sequence of insulin-like peptide from toadfish."

( x i ) SEQUENCE DESCRIPTION: SEQ ID NO:4:

```
Gly Ile Val Glu Gln Cys Cys His Arg Pro Cys Asp Lys Phe Asp Leu
1               5                   10                  15
Gln Ser Tyr Cys Asn
            20
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Geodia cydomium ( i x ) FEATURE:
        ( A ) NAME/KEY: Peptide
        ( B ) LOCATION: 1..19
        ( D ) OTHER INFORMATION: /label=peptide
            / note="Amino-terminal sequence of insulin-like
            peptide from Geodia cydornium."

( x i ) SEQUENCE DESCRIPTION: SEQ ID NO:5:

```
Ile Val Gln Gln Cys Thr Ser Gly Ile Cys Ser Leu Tyr Gln Glu Asn
1               5                   10                  15
Tyr Cys Asn
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Neurospora ( i x ) FEATURE:
        ( A ) NAME/KEY: Peptide
        ( B ) LOCATION: 1..22
        ( D ) OTHER INFORMATION: /label=peptide
            / note="Amino-terminal sequence of insulin-like
            peptide from Neurospora crassa."

( x i ) SEQUENCE DESCRIPTION: SEQ ID NO:6:

```
Leu Phe Ser Pro Ser Cys Ser Asp Leu Trp Thr His Thr Ile Val Glu
1               5                   10                  15
Asn Tyr Leu Tyr Asn Leu
            20
```

( 2 ) INFORMATION FOR SEQ ID NO:7:

( i ) SEQUENCE CHARACTERISTICS:
        ( A ) LENGTH: 30 base pairs (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i x) FEATURE:
                (A) NAME/KEY: -
                (B) LOCATION: 1..30
                (D) OTHER INFORMATION: /label=oligonucleotide
                    / note="used for screening Saccharomyces genomic
                    library for clones encoding insulin-like peptide"

(i x) FEATURE:
                (A) NAME/KEY: modified_base
                (B) LOCATION: 1..30
                (D) OTHER INFORMATION: /note="residues marked as "n" in
                    the sequence are inosine."

(x i) SEQUENCE DESCRIPTION: SEQ ID NO:7:

GARAARGCNG CNYTNCARAC NTAYTGYAAY					30

(2) INFORMATION FOR SEQ ID NO:8:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i x) FEATURE:
                (A) NAME/KEY: -
                (B) LOCATION: 1..15
                (D) OTHER INFORMATION: /label=oligonucleotide
                    / note="degenerate oligonucleotide used to screen
                    Saccharomyces genomic library for genes encoding
                    insulin- like peptide"

(x i) SEQUENCE DESCRIPTION: SEQ ID NO:8:

GTNTGGCCNA CNGAT					15

(2) INFORMATION FOR SEQ ID NO:9:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (i i) MOLECULE TYPE: DNA (genomic)

(i i i) HYPOTHETICAL: NO (i x) FEATURE:
                (A) NAME/KEY: -
                (B) LOCATION: 1..15
                (D) OTHER INFORMATION: /label=oligonucleotide
                    / note="degenerate oligonucleotide used to screen
                    Saccharomyces genomic library for genes encoding
                    insulin- like peptide"

(x i) SEQUENCE DESCRIPTION: SEQ ID NO:9:

GTNTGGCCNA CNAAC					15

(2) INFORMATION FOR SEQ ID NO:10:

(i) SEQUENCE CHARACTERISTICS:

(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: -
(B) LOCATION: 1..15
(D) OTHER INFORMATION: /label=oligonucleotide
/ note="degenerate oligonucleotide used to screen Saccharomyces genomic library for genes encoding insulin- like peptide"

(xi) SEQUENCE DESCRIPTION: SEQ ID NO:10:

GTNTGGCCNA CNAAT       15

(2) INFORMATION FOR SEQ ID NO:11:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Saccharomyces cerevisiae (xi) SEQUENCE DESCRIPTION: SEQ ID NO:11:

Val Gly Val Trp Pro Thr Asp Cys Ser His Tyr Ala Ala Glu Lys Ala
1               5                   10                  15

Ala Leu Gln Thr Tyr Cys Asn
            20

(2) INFORMATION FOR SEQ ID NO:12:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Saccharomyces cerevisiae (xi) SEQUENCE DESCRIPTION: SEQ ID NO:12:

Ala Gly Val Trp Pro Thr Asp Cys Ser His Tyr Ala Ala Glu Lys Ala
1               5                   10                  15

Ala Leu Gln Thr Tyr Cys Asn
            20

(2) INFORMATION FOR SEQ ID NO:13:

(i) SEQUENCE CHARACTERISTICS:
(A) LENGTH: 24 amino acids
(B) TYPE: amino acid
(C) STRANDEDNESS: single (D) TOPOLOGY: linear (ii) MOLECULE TYPE: peptide (iii) HYPOTHETICAL: NO (v) FRAGMENT TYPE: N-terminal (vi) ORIGINAL SOURCE:
    (A) ORGANISM: Saccharomyces cerevisiae (xi) SEQUENCE DESCRIPTION: SEQ ID NO:13:

```
Val Gly Val Trp Pro Thr Asp Cys Ser His Tyr Ala Cys Ala Glu Lys
1               5                   10                  15
Ala Ala Leu Gln Thr Tyr Cys Asn
            20
```

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Saccharomyces cerevisiae (xi) SEQUENCE DESCRIPTION: SEQ ID NO:14:

```
Val Gly Val Trp Pro Thr Asp Cys Ser His Tyr Ala Ala Glu Ser Ala
1               5                   10                  15
Ala Leu Gln Thr Tyr Cys Asn
            20
```

(2) INFORMATION FOR SEQ ID NO:15:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Saccharomyces cerevisiae (xi) SEQUENCE DESCRIPTION: SEQ ID NO:15:

```
Val Gly Val Trp Pro Thr Asp Cys Ser His Tyr Ala Ala Glu Leu Ala
1               5                   10                  15
Ala Leu Gln Thr Tyr Cys Asn
            20
```

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS: single
        (D) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:16:

```
Val Gly Val Trp Pro Thr Asp Cys Ser His Tyr Ala Ala Glu Lys Ala
 1               5                  10                  15
Ala Leu Gln Thr Tyr Pro Asn
                20
```

( 2 ) INFORMATION FOR SEQ ID NO:17:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:17:

```
Ala Gly Val Trp Pro Thr Asp Cys Ser His Tyr Ala Cys Ala Glu Lys
 1               5                  10                  15
Ala Ala Leu Gln Thr Tyr Cys Asn
                20
```

( 2 ) INFORMATION FOR SEQ ID NO:18:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:18:

```
Ala Gly Val Trp Pro Thr Asp Cys Ser His Tyr Ala Ala Glu Ser Ala
 1               5                  10                  15
Ala Leu Gln Thr Tyr Cys Asn
                20
```

( 2 ) INFORMATION FOR SEQ ID NO:19:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
      ( A ) ORGANISM: Saccharomyces cerevisiae ( x i ) SEQUENCE DESCRIPTION: SEQ ID NO:19:

```
Ala  Gly  Val  Trp  Pro  Thr  Asp  Cys  Ser  His  Tyr  Ala  Ala  Glu  Leu  Ala
1                   5                        10                       15

Ala  Leu  Gln  Thr  Tyr  Cys  Asn
                    20
```

( 2 ) INFORMATION FOR SEQ ID NO:20:

( i ) SEQUENCE CHARACTERISTICS:
      ( A ) LENGTH: 23 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
      ( A ) ORGANISM: Saccharomyces cerevisiae ( x i ) SEQUENCE DESCRIPTION: SEQ ID NO:20:

```
Ala  Gly  Val  Trp  Pro  Thr  Asp  Cys  Ser  His  Tyr  Ala  Ala  Glu  Lys  Ala
1                   5                        10                       15

Ala  Leu  Gln  Thr  Tyr  Pro  Asn
                    20
```

( 2 ) INFORMATION FOR SEQ ID NO:21:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
      ( A ) ORGANISM: Saccharomyces cerevisiae ( x i ) SEQUENCE DESCRIPTION: SEQ ID NO:21:

```
Val  Gly  Val  Trp  Pro  Thr  Asp  Cys  Ser  His  Tyr  Ala  Cys  Ala  Glu  Ser
1                   5                        10                       15

Ala  Ala  Leu  Gln  Thr  Tyr  Cys  Asn
                    20
```

( 2 ) INFORMATION FOR SEQ ID NO:22:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO (v) FRAGMENT TYPE: N-terminal (vi) ORIGINAL SOURCE:
    (A) ORGANISM: Saccharomyces cerevisiae (xi) SEQUENCE DESCRIPTION: SEQ ID NO:22:

```
Val Gly Val Trp Pro Thr Asp Cys Ser His Tyr Ala Cys Ala Glu Leu
1               5                   10                  15
Ala Ala Leu Gln Thr Tyr Cys Asn
            20
```

(2) INFORMATION FOR SEQ ID NO:23:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Saccharomyces cerevisiae (xi) SEQUENCE DESCRIPTION: SEQ ID NO:23:

```
Ala Gly Val Trp Pro Thr Asp Cys Ser His Tyr Ala Cys Ala Glu Ser
1               5                   10                  15
Ala Ala Leu Gln Thr Tyr Cys Asn
            20
```

(2) INFORMATION FOR SEQ ID NO:24:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Saccharomyces cerevisiae (xi) SEQUENCE DESCRIPTION: SEQ ID NO:24:

```
Ala Gly Val Trp Pro Thr Asp Cys Ser His Tyr Ala Cys Ala Glu Leu
1               5                   10                  15
Ala Ala Leu Gln Thr Tyr Cys Asn
            20
```

(2) INFORMATION FOR SEQ ID NO:25:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:25:

```
Val  Gly  Val  Trp  Pro  Thr  Asp  Cys  Ser  His  Tyr  Ala  Cys  Ala  Glu  Lys
1                   5                        10                       15

Ala  Ala  Leu  Gln  Thr  Tyr  Pro  Asn
               20
```

( 2 ) INFORMATION FOR SEQ ID NO:26:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:26:

```
Ala  Gly  Val  Trp  Pro  Thr  Asp  Cys  Ser  His  Tyr  Ala  Cys  Ala  Glu  Lys
1                   5                        10                       15

Ala  Ala  Leu  Gln  Thr  Tyr  Pro  Asn
               20
```

( 2 ) INFORMATION FOR SEQ ID NO:27:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:27:

```
Val  Gly  Val  Trp  Pro  Thr  Asp  Cys  Ser  His  Tyr  Ala  Cys  Ala  Glu  Ser
1                   5                        10                       15

Ala  Ala  Leu  Gln  Thr  Tyr  Pro  Asn
               20
```

( 2 ) INFORMATION FOR SEQ ID NO:28:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:28:

Val Gly Val Trp Pro Thr Asp Cys Ser His Tyr Ala Cys Ala Glu Leu
1               5                   10                  15

Ala Ala Leu Gln Thr Tyr Pro Asn
            20

( 2 ) INFORMATION FOR SEQ ID NO:29:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:29:

Ala Gly Val Trp Pro Thr Asp Cys Ser His Tyr Ala Cys Ala Glu Ser
1               5                   10                  15

Ala Ala Leu Gln Thr Tyr Pro Asn
            20

( 2 ) INFORMATION FOR SEQ ID NO:30:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:30:

Ala Gly Val Trp Pro Thr Asp Cys Ser His Tyr Ala Cys Ala Glu Leu
1               5                   10                  15

Ala Ala Leu Gln Thr Tyr Pro Asn
            20

( 2 ) INFORMATION FOR SEQ ID NO:31:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Saccharomyces cerevisiae ( x i ) SEQUENCE DESCRIPTION: SEQ ID NO:31:

```
              Val   Gly   Val   Trp   Pro   Thr   Asp   Cys   Ser   His   Tyr   Ala   Ala   Glu   Ser   Ala
              1                       5                             10                            15

Ala   Leu   Gln   Thr   Tyr   Pro   Asn
                                20
```

( 2 ) INFORMATION FOR SEQ ID NO:32:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:32:

```
              Val   Gly   Val   Trp   Pro   Thr   Asp   Cys   Ser   His   Tyr   Ala   Ala   Glu   Leu   Ala
              1                       5                             10                            15

Ala   Leu   Gln   Thr   Tyr   Pro   Asn
                                20
```

( 2 ) INFORMATION FOR SEQ ID NO:33:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:33:

```
              Ala   Gly   Val   Trp   Pro   Thr   Asp   Cys   Ser   His   Tyr   Ala   Ala   Glu   Ser   Ala
              1                       5                             10                            15

Ala   Leu   Gln   Thr   Tyr   Pro   Asn
                                20
```

( 2 ) INFORMATION FOR SEQ ID NO:34:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Saccharomyces cerevisiae ( x i ) SEQUENCE DESCRIPTION: SEQ ID NO:34:

```
              Ala   Gly   Val   Trp   Pro   Thr   Asp   Cys   Ser   His   Tyr   Ala   Ala   Glu   Leu   Ala
```

```
      1             5                10              15
Ala Leu Gln Thr Tyr Pro Asn
              20
```